(12) United States Patent  (10) Patent No.: US 8,992,220 B2
Berger  (45) Date of Patent: Mar. 31, 2015

(54) DENTAL BRIDGE ATTACHMENT SYSTEM AND METHOD

(75) Inventor: Uzi Berger, Hod Hasharon (IL)

(73) Assignee: Dental Innovision Ltd, Road Town, Tortola (VG)

( * ) Notice: Subject to any disclaimer, the term of this patent is extended or adjusted under 35 U.S.C. 154(b) by 0 days.

(21) Appl. No.: 13/394,554

(22) PCT Filed: Sep. 7, 2010

(86) PCT No.: PCT/IL2010/000743
§ 371 (c)(1),
(2), (4) Date: Mar. 7, 2012

(87) PCT Pub. No.: WO2011/030342
PCT Pub. Date: Mar. 17, 2011

(65) Prior Publication Data
US 2012/0171639 A1    Jul. 5, 2012

Related U.S. Application Data

(60) Provisional application No. 61/240,805, filed on Sep. 9, 2009.

(51) Int. Cl.
*A61C 8/00* (2006.01)
*A61C 13/273* (2006.01)
(52) U.S. Cl.
CPC ............... *A61C 8/0048* (2013.01); *A61C 8/005* (2013.01); *A61C 13/273* (2013.01)
USPC ........................................................ 433/173
(58) Field of Classification Search
USPC .................. 433/172–176, 181, 182, 191–195
See application file for complete search history.

(56) References Cited

U.S. PATENT DOCUMENTS 4,085,506 A * 4/1978 Lew ............................. 433/172
4,931,916 A   6/1990 Callahan
(Continued)

FOREIGN PATENT DOCUMENTS

CN   1424894 A   6/2003
CN   101146490 A  3/2008
(Continued)

OTHER PUBLICATIONS

The International Search Report for International Application No. PCT/IL2010/000743, mailed on Apr. 14, 2011; published as WO 2011/030342 A3 on Jun. 3, 2011, seven pages.

*Primary Examiner* — Ralph Lewis
(74) *Attorney, Agent, or Firm* — Vorys, Sater, Seymour and Pease LLP; Susanne M. Hopkins; William L. Klima

(57) ABSTRACT

Provided is a removable bridge system for attachment to a plurality of dental implants, including a plurality of abutments, each including a seat portion conforming with a shape of a corresponding implant head and allowing fixedly positioning of the abutment to the implant, and an abutment head. At least one of the abutments is configured as a locking abutment and includes a locking portion. A bridge generally conforming with dental parameters of the individual has a bottom surface formed with a receiving apertures shaped so as to snugly fit over a corresponding abutment head. The bridge further includes a locking arrangement for removably locking the bridge to the abutments, and including one or more locks for detachable locking to a respective at least one locking abutment.

29 Claims, 16 Drawing Sheets

(56) References Cited

U.S. PATENT DOCUMENTS

| | | |
|---|---|---|
| 5,057,017 A | 10/1991 | Sillard |
| 5,135,395 A | 8/1992 | Marlin |
| 5,234,341 A | 8/1993 | Johansen |
| 5,527,182 A | 6/1996 | Willoughby |
| 5,564,291 A | 10/1996 | Tsai |
| 5,667,384 A | 9/1997 | Sutter et al. |
| 5,716,214 A | 2/1998 | Lund et al. |
| 5,873,721 A * | 2/1999 | Willoughby .................. 433/173 |
| 6,012,923 A | 1/2000 | Bassett et al. |
| 6,048,203 A * | 4/2000 | Rosenberg ................... 433/173 |
| 6,283,753 B1 | 9/2001 | Willoughby |
| 6,322,364 B1 * | 11/2001 | Oshida et al. ................. 433/173 |
| 6,788,986 B1 | 9/2004 | Traber et al. |
| 7,101,183 B2 | 9/2006 | Augthun et al. |
| 2006/0106484 A1 | 5/2006 | Saliger et al. |
| 2006/0223029 A1 * | 10/2006 | Berger ........................... 433/172 |
| 2007/0224574 A1 * | 9/2007 | Poirier ............................ 433/75 |
| 2008/0038694 A1 | 2/2008 | Tache et al. |
| 2008/0227057 A1 | 9/2008 | Anitua Aldecoa |

FOREIGN PATENT DOCUMENTS

| | | |
|---|---|---|
| JP | 4-341257 A | 11/1992 |
| JP | 5-23356 | 2/1993 |
| JP | 8-47500 A | 2/1996 |

* cited by examiner

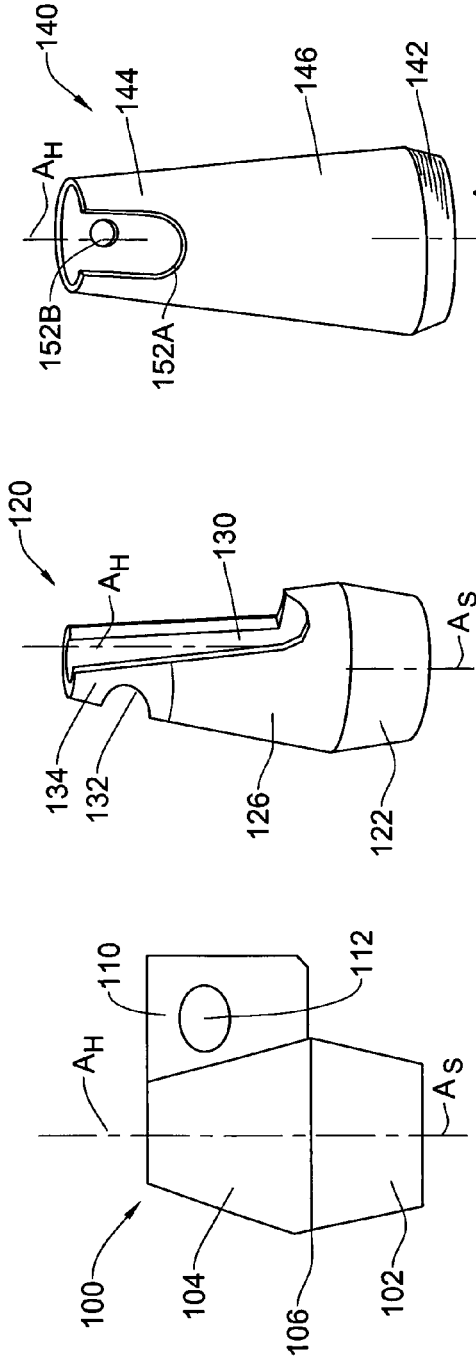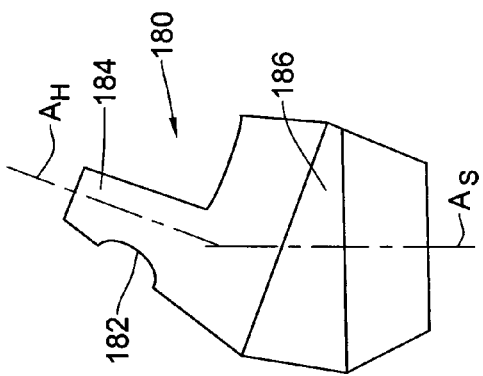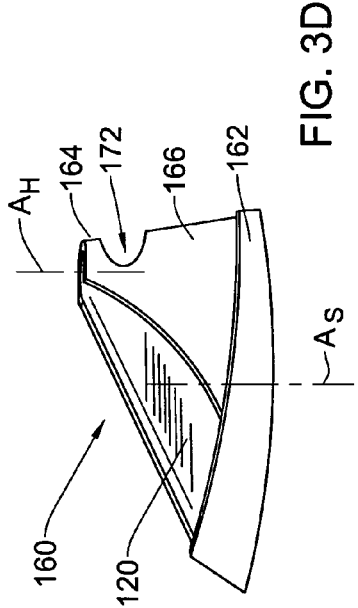

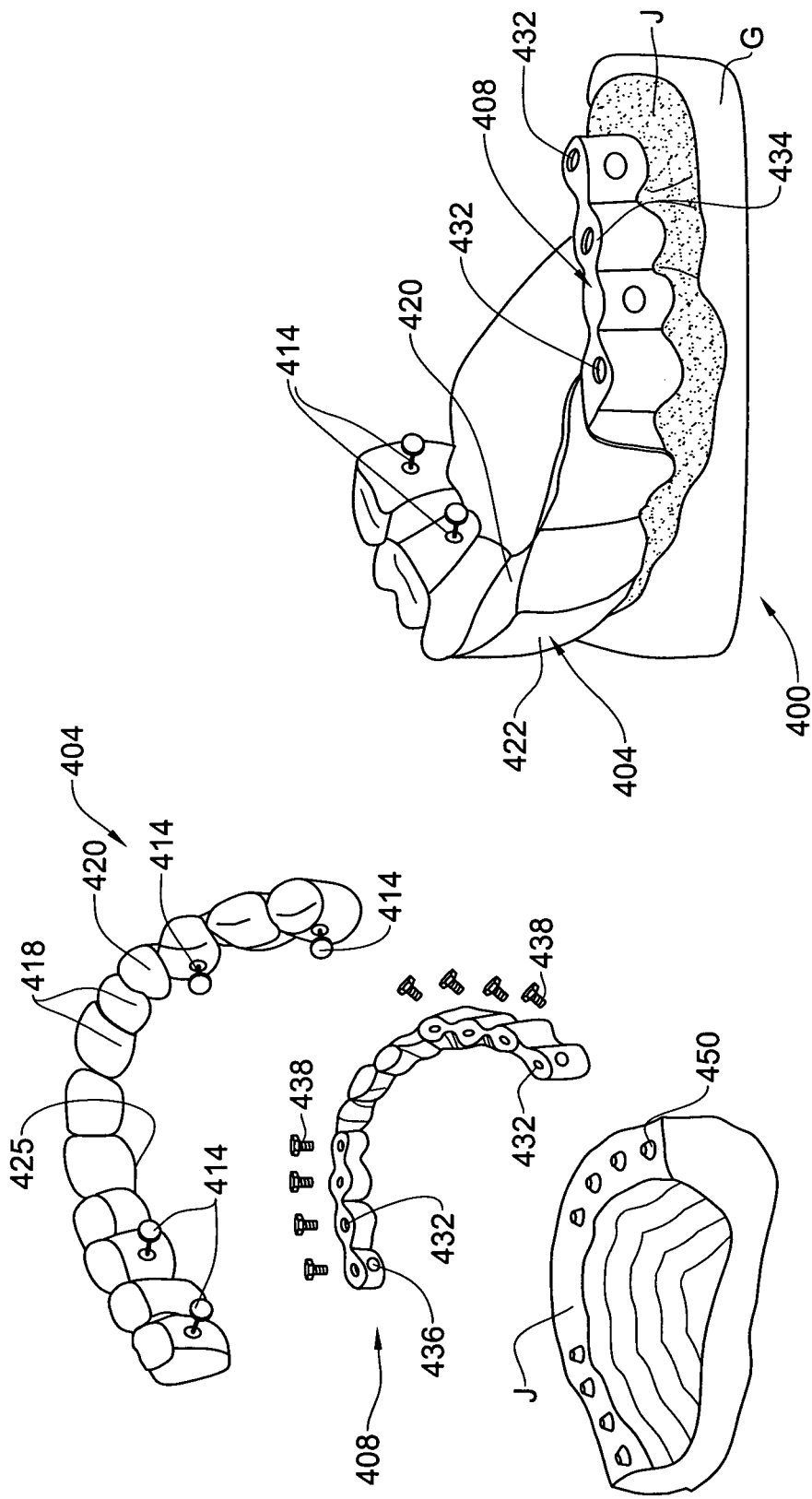

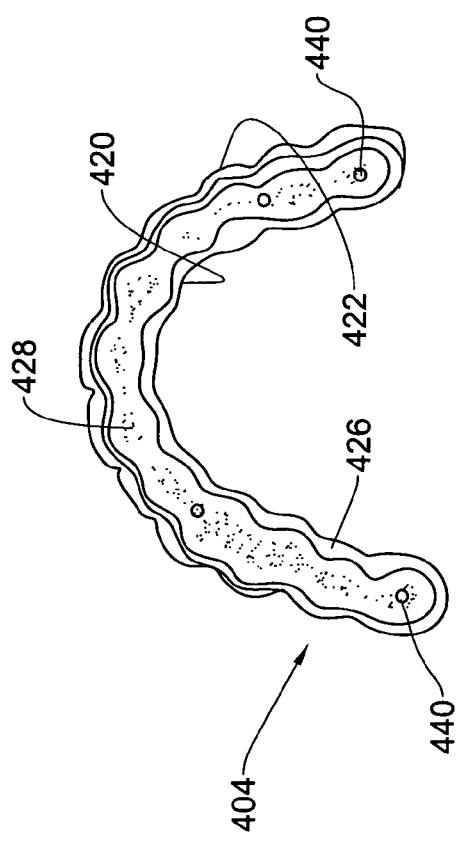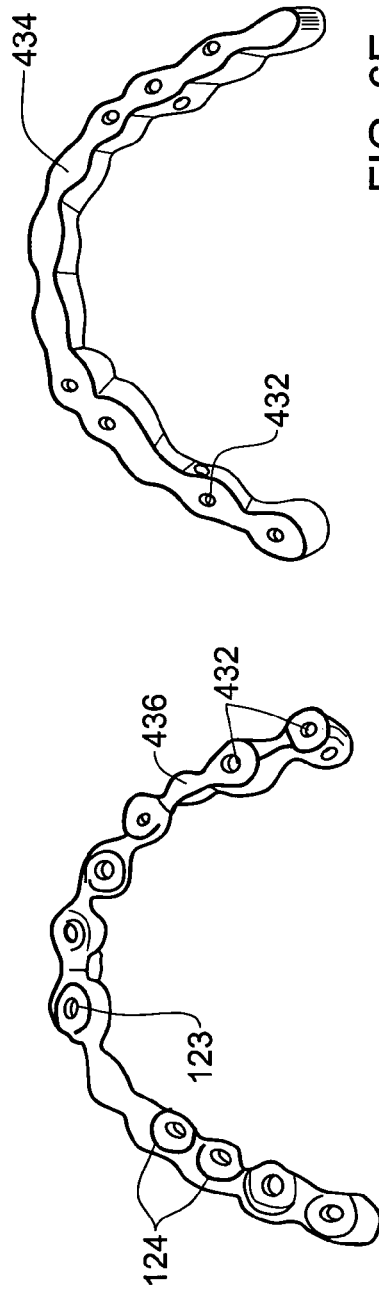
FIG. 6C
FIG. 6E
FIG. 6D

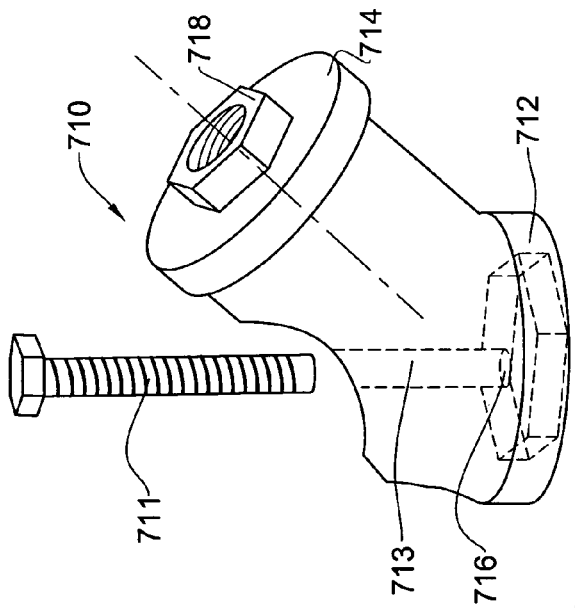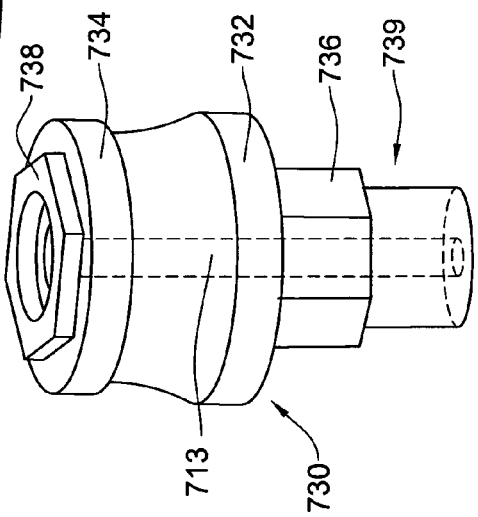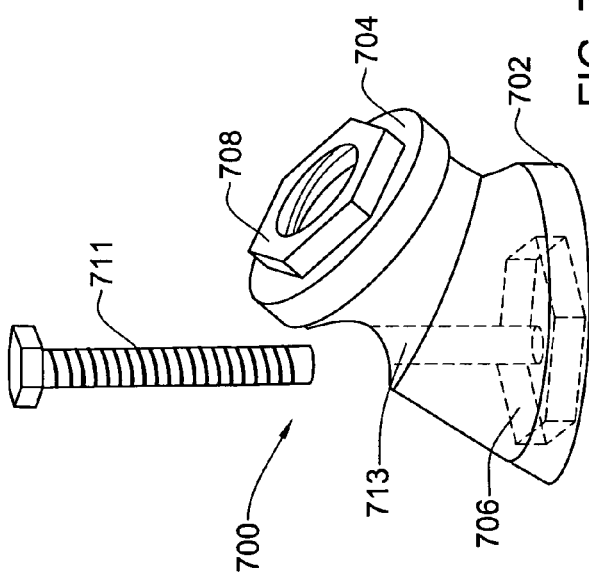

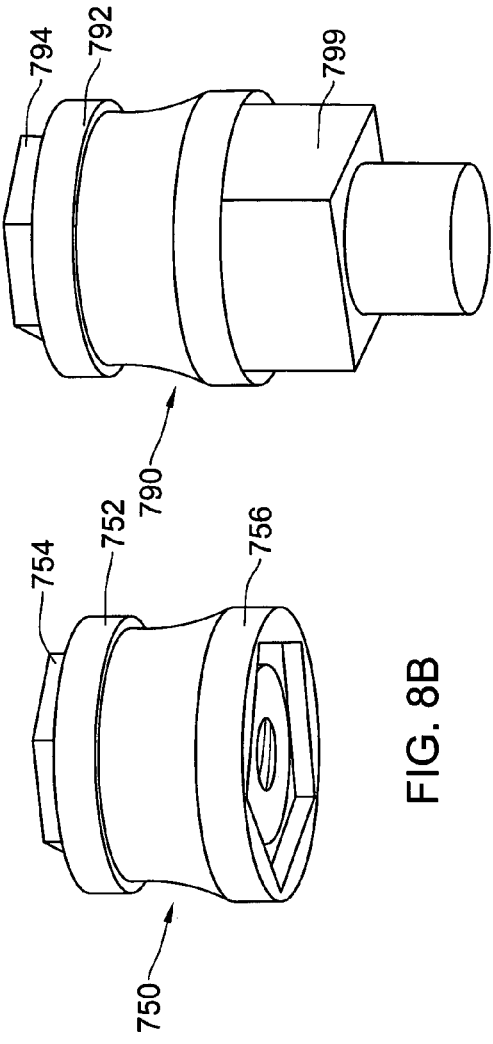
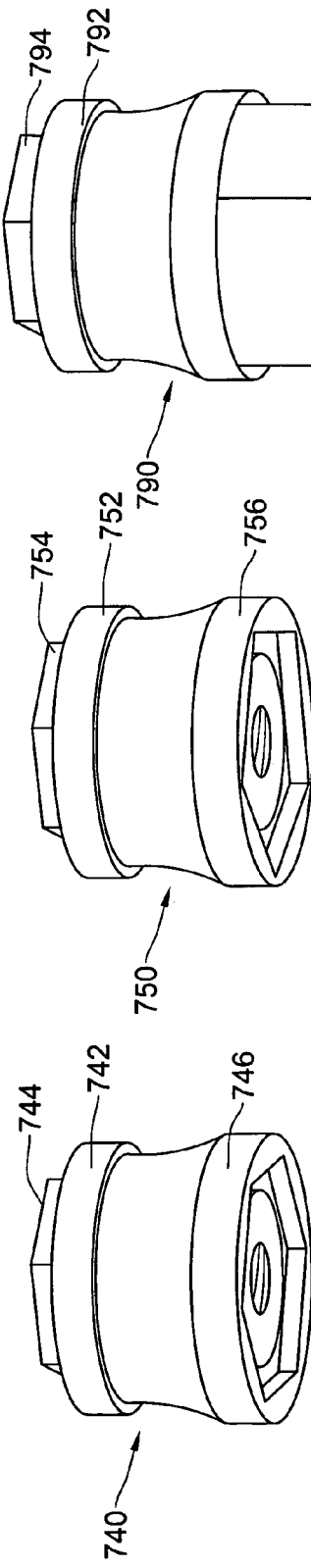
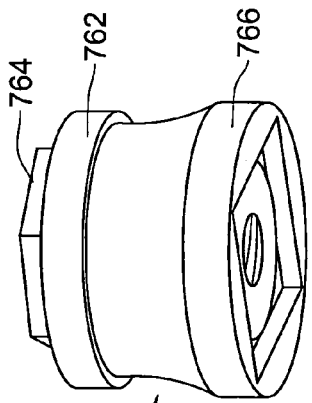
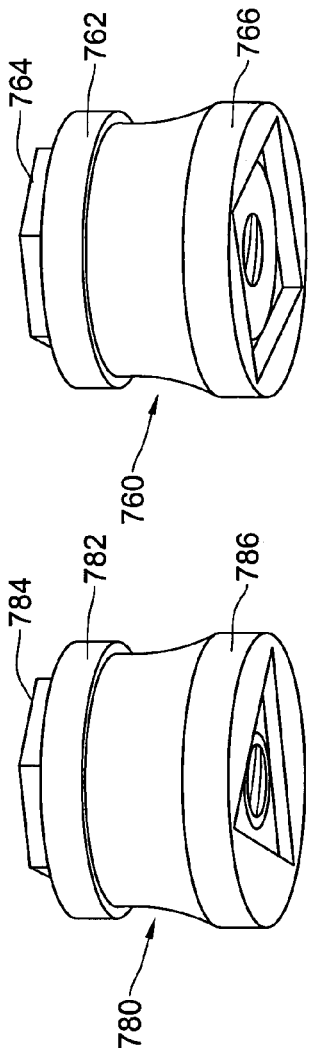
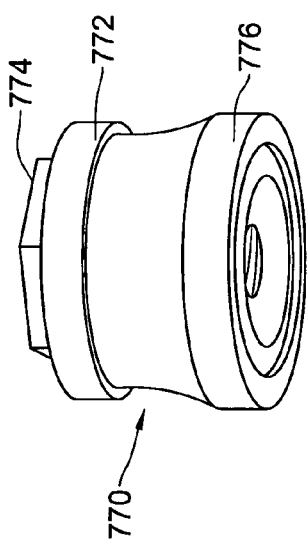

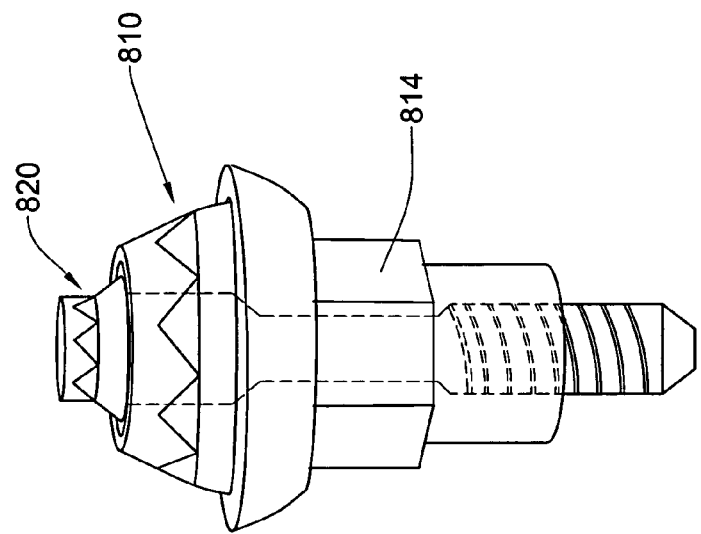
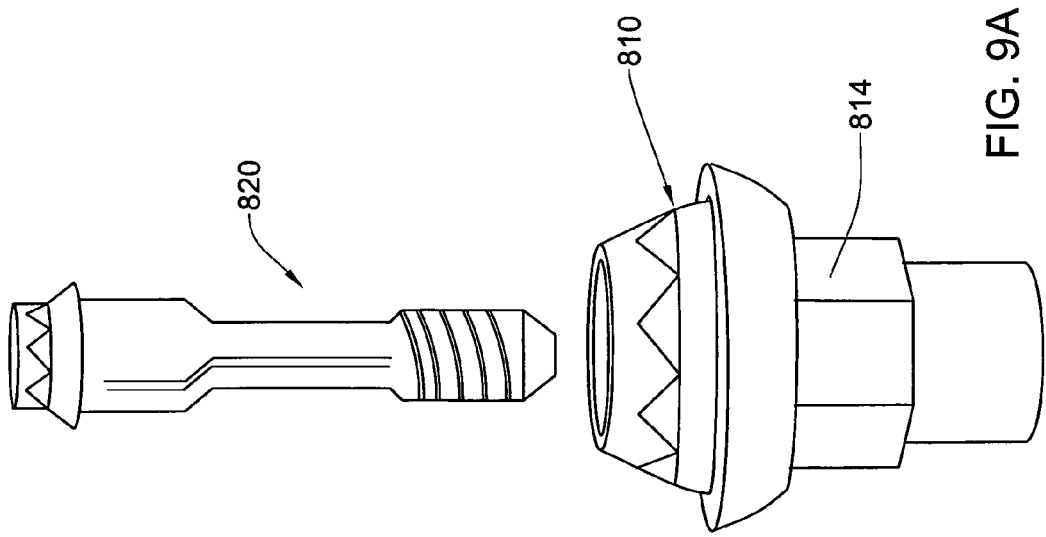

DENTAL BRIDGE ATTACHMENT SYSTEM AND METHOD

This is a National Phase Application filed under 35 U.S.C. §371 as a national stage of PCT/IL2010/000743, filed on Sep. 7, 2010, an application claiming the benefit under 35 U.S.C. §119(e) of U.S. Provisional Application No. 61/240,805, filed on Sep. 9, 2009, the content of each of which is hereby incorporated by reference in their entirety.

FIELD OF THE INVENTION

The present disclosed subject matter is concerned with a system and a method for attachment of a dental bridge to dental implants of an individual.

BACKGROUND OF THE INVENTION

Partial or complete loss of an individual's natural teeth, either or both at the upper and lower jaw, due to age, accident, diseases or other reasons has some serious effects on an individual, both functionally and socially. Lack of teeth poses several serious functional problems such as distortion of the individual's face, not being able to chew, speech difficulties, etc. Even more so, a smile with a full set of white teeth is considered something to be desired, i.e. esthetics play an important role. These problems become more severe depending on the number of missing teeth.

Utilization of artificial denture appliance poses a general problem concerned with retention of same in position as during normal chewing or talking, the appliance may have the tendency to ride up out of its position, causing speech difficulties, chewing difficulties, spitting and other social unpleasant situations, resulting in general unsatisfactory.

The term dental bridge (often simply referred to as bridges) as used herein the specification and claims denotes an integrated array of artificial teeth mimicking the teeth of a individual and designed for anchoring over two or more studs fixed to the individual's jaw bone (mandibular or maxillar), without the skirt portion, i.e. the gum mimicking portion (at times referred to as an 'acrylic flange'). The term mimicking suggests that the bridge follows the individual's anatomical parameters, such as shape, size, color etc.

The terms studs and implants are used interchangeably throughout the specification and claims.

A challenge in this field is designing and manufacturing the bridge so as to achieve perfect fitting thereof to the particular needs and anatomical parameters of the individual.

There are known personalized dentures, such as, for example, U.S. Pat. No. 2006/0223029, disclosing a removable denture system comprising a support beam fixedly attached to the individual's alveolar ridge above the mucous membrane by a plurality of dental implants, and a denture generally conforming with the dental parameters of the individual and integrated with a super-structure. The super-structure comprises at least a portion shaped in confirmation with the support beam, and a denture locking arrangement for removably, though fixedly articulating the denture to the support beam preventing unintentional disengagement of the denture.

Dental bridges are known to be fixed to implants by means of connecting elements, referred to as 'abutments', or by direct fixing thereof to the implants. An abutment is usually fastened to the implant at its one end and to a bridge or another element at its other end. In the installed state the abutments are usually invisible or visible to a limited degree in the patient's mouth. One example of such abutments is disclosed in U.S. Pat. No. 6,788,986.

SUMMARY OF THE INVENTION

The present disclosed subject matter is concerned, according to a first aspect thereof, with a dental bridge configured for fixedly detachable anchorage over the studs, i.e. in a fashion facilitating fast and easy mounting yet fixedly supporting so as to obtain a sturdy and secure engagement to the studs, and however suited for easy removal.

According to this aspect of the present disclosed subject matter there is provided a removable bridge system for attachment to a plurality of dental implants, each implant having an implant body fixedly received inside a jawbone of an individual and an implant head projected from said jawbone. The system comprises:

a plurality of abutments, each comprising a seat portion formed with a shape conforming with a shape of a corresponding implant head and allowing fixedly positioning of the abutment to the implant, and an abutment head; at least one of said abutments is configured as a locking abutment and comprises a locking portion;

a bridge generally conforming with dental parameters of the individual, having a bottom surface formed with a receiving apertures, each aperture shaped so as to snugly fit, at high tolerance, over a corresponding abutment head; and the bridge further comprises a locking arrangement for removably locking the to bridge to said abutments, and comprising one or more locks for detachable locking to a respective at least one locking abutment.

The load applied through the bridge while chewing is fully born by the abutments and directed to the studs (and further to the bone tissue), whilst the one or more locks substantially do not bear any loads. Furthermore, the tolerance between the receiving apertures of the bridge and the respective abutment heads is tight, so as to reduce, or substantially eliminate any tolerance and respective motion therebetween. However, removal of the bridge is facilitated substantially without the need of any tools.

It is further noted that whilst the locking mechanism in itself does not bear loads (i.e. a locking pin, where provided is not subject to any loads), the housing of the locking mechanism may function as a receiving aperture configured for snugly bearing over the locking abutment.

The present invention disclosed subject matter further calls for a method for applying a patient with a dental bridge at a removably secured fashion, the method comprises the following steps:

fixing at least two implants inside a jawbone of the individual, each having an implant body fixedly received within the jawbone and an implant head projected from said jawbone;

obtaining a plurality of abutments each comprising a seat formed with a shape conforming with a shape of a corresponding implant head, and an abutment head, wherein at least one of said abutments is configured as a locking abutment and comprises a locking portion. Fixing said seat portions of the abutments over said implant heads;

providing a bridge generally conforming with dental parameters of the individual, having a bottom surface configured with a plurality of receiving apertures, each conforming at high tolerance with the shape of a respective abutment. Said bridge further configured with at least one lock for detachable locking to a respective at least one locking abutment;

snugly fitting said bridge over corresponding abutment heads and locking/unlocking the locking arrangement.

Any one or more of the following features and designs may be incorporated in the bridge system and method in accordance with the present disclosed subject matter:

The locking arrangement comprises at least one and typically two or more locks for releasable locking engagement;

The seat portion of the abutments extends about a fixation bore (for securing thereof to the implants by abutment screws) configured with an inner shape corresponding with an outer shape of the implant head;

The seat portion of the abutments may be of any regular or irregular shape;

The abutments are made of any rigid, metallic or non-metallic material (such as, for example, metals—gold, titanium, chrome-cobalt, zirconium, porcelain, plastic/acrylic/polymeric materials, composite materials, and combinations thereof);

The bridge is made of any rigid, metallic or non-metallic material (such as, for example, metals—gold, titanium, chrome-cobalt, zirconium, porcelain, plastic/acrylic/polymeric materials, composite materials, and combinations thereof);

The locking arrangement comprises any type of one or more locks such as swivel-type, magnet based locks, locators, or any other type of locking mechanism;

According to one example the locks are a pin-type locks, each lock configured with a locking pin displaceable through either a rear face (lingual face) or a front face (labial face) of the bridge, between a locked position in which it arrests a locking bore configured at the locking portion of a respective locking abutment (wherein the bridge is prevented from displacement about a path of insertion thereof), and un-locked position where it is disengaged from said locking portion (and whereby the bridge may be removed along its path of insertion);

An ejection bore may extend across the abutment and dental bridge, coaxial with the locking pin, to assist in displacing the pin into the unlocked position;

The bridge system may be mounted over an adapter abutment to be received between the seat portion of the abutment and the implant head. This option is especially useful when the gum tissue is relatively high, or when angular adjustment is required respective to a longitudinal axial of a respective dental implant;

According to another aspect of the present disclosed subject matter there is disclosed an adapter abetment to be received between the seat portion of the abutment and the implant head. This option is especially useful when the gum tissue is relatively high, or when angular adjustment is required respective to a longitudinal axial of a respective dental implant.

Even more so, the adapter abetment is suitable for coupling and interconnecting between different types of different implant systems.

The adapter abutment is configured with an adapter seat portion configured for motionless fixation over a dental implant head and defining an adapter seat portion axis, and an adapter head portion configured for motionless affixing thereto a seat portion of an abutment, and defining an adapter head portion axis; with an adapter abutment body portion extending between said adapter seat portion and said adapter head portion. However, the head portion of an adapter abutment may also be suited for directly supporting the bridge.

Any one or more of the following features and designs may be incorporated in an adapter abutment in accordance with the present disclosed subject matter:

The adapter seat portion axis and the adapter head portion axis may coextend or may be parallel to one another though non-coaxial, or intersect one another;

The adapter abutment body portion may extend coaxial with any of the said adapter seat portion and said adapter head portion;

Each of the adapter seat portion and the adapter head portion may be of any regular or irregular shape;

Each of the adapter seat portion and the adapter head portion may be configures as either a mail-type coupler (referred to in the art as 'internal connection) or a female-type coupler (referred to in the art as 'external connection), configured for fixedly coupling engagement, at fixed angular orientation, with respect to a dental implant head and a seat portion of an abutment, respectively. It is noted that the phrase hex refers in fact to any polygonal shape;

The adapter seat portion and the adapter head portion may be identical couple-types or different coupler-types;

The adapter abutment may be secured over the head of a standard abutment and further to the dental implant head using a single fastener screw;

An abutment may be secured directly over the adapter head portion, and/or via a fastener screw.

The adapter abutment, at an assembled position of the dental bridge, are fully received and concealed within the dental bridge;

The adapter abutment may comprise a locking portion, for locking engagement with a locking arrangement;

The adapter abutment allows to extend (elongate) the implant to a desired height and at a desired angle with respect to the implant, so as to allow convenient fixation of elements such as abutments and unitary braces described above, or other elements adapted to be fixed on the dental implants.

According to another aspect of the present disclosed subject matter there is provided a bridge system for attachment to a jawbone of an individual, the system comprising:

a plurality of dental implants, each configured with an implant body for fixedly receiving inside the jawbone, and an implant head projected from said jawbone;

a Reduced Bridge-Core made of rigid material and configured for fixedly mounting and securing to the plurality of dental implants over the implant heads, or over abutments (secured in turn to the dental implants);

a Super Dental-Bridge generally conforming with the dental parameters of the individual, and formed with a bottom surface having a recess extending substantially there along; the Super Dental-Bridge is adapted for snugly receiving said Reduced Bridge-Core within said recess at a tight fit; and a fixing arrangement for fixing said Super Dental-Bridge to said Reduced Bridge-Core.

The load applied through the Super Dental-Bridge while chewing is fully born by the Reduced Bridge-Core and is then directed to the abutments and further to the studs to the bone tissue, whilst the one or more locks substantially do not bear any loads.

Furthermore, the tolerance between the receiving apertures of the Super Dental-Bridge and the respective Reduced Bridge-Core is tight, so as to reduce, or substantially eliminate any tolerance and respective motion therebetween.

However, when using locator-type locking mechanisms (or similar type locking mechanisms), axially directed loads only, are transferred through a longitudinal axis of the locator.

It is further noted that whilst the locking mechanism in itself does not bear loads (i.e. a locking pin, where provided is not subject to any loads), the housing of the locking mechanism may function as a receiving aperture configured for snugly bearing over the locking abutment.

Any one or more of the following features and designs may be applied to the bridge system in accordance with the present disclosed subject matter described above:

- The Reduced Bridge-Core is a unitary element and continuously extends within the Super Dental-Bridge;
- The recess configured at the bottom surface of the Super Dental-Bridge is continuous;
- The recess configured at the bottom surface of the Super Dental-Bridge is deeper than the height of the Reduced Bridge-Core, such that at the assembled position, when the Super Dental-Bridge is mounted over the Reduced Bridge-Core, the later is concealed by the Super Dental-Bridge;
- The Reduced Bridge-Core is configured in a shape simulating the individual's dental parameters, and his teeth, though at reduced scale;
- Base portions of the Reduced Bridge-Core conform with the shape of respective implant heads, and configured for fixedly securing thereto;
- The reduced bridge is configured for fixedly securing directly over the implant heads, or over abutments which in turn are fixed to the implants;
- The Reduced Bridge-Core is made of any rigid, metallic or non-metallic material (such as, for example, metals—gold, titanium, chrome-cobalt, zirconium, porcelain, plastic/acrylic/polymeric materials, composite materials, and combinations thereof);
- The Super Dental-Bridge is made of any rigid, metallic or non-metallic material (such as, for example, metals—gold, titanium, chrome-cobalt, zirconium, porcelain, plastic/acrylic/polymeric materials, composite materials, and combinations thereof). When the material of which the Super Dental-Bridge is a structural material, there is need to apply thereto a finishing layer mimicking the shape, size, color and texture of the natural teeth;
- The fixing arrangement may be a locking mechanism facilitating repeatable locking/unlocking of the Super Dental-Bridge over the Reduced Bridge-Core, where removal of the Super Dental-Bridge is facilitated by the individual, or a fixed securing arrangement, where removal of the Super Dental-Bridge is facilitated by dentist rather than by the individual;
- Where there is provided a locking mechanism facilitating repeatable locking/unlocking of the Super Dental-Bridge over the Reduced Bridge-Core, there may be provided, within the Super Dental-Bridge, a reinforcement structure configured for supporting the one or more locking mechanisms within the Super Dental-Bridge;
- A fixed securing arrangement may be an adhesive/bonding agent applied between the Super Dental-Bridge and the Reduced Bridge-Core, or fasteners such screws and the like.
- A locking mechanism may be any type of one or more locks such as swivel-type, magnet based locks, locators, etc.;
- There are one or more locks, being pin-type locks, each lock configured with a locking pin displaceable through either a rear face (lingual face) or a front face (labial face) of the Super Dental-Bridge, between a locked position in which it arrests a locking bore configured at the locking portion of a respective locking abutment (wherein the bridge is prevented from displacement about a path of insertion thereof), and un-locked position where it is disengaged from said locking portion (and whereby the bridge may be removed along its path of insertion);
- An ejection bore may extend across the abutment and Super Dental-Bridge, coaxial with the locking pin, to assist in displacing the pin into the unlocked position;

BRIEF DESCRIPTION OF THE DRAWINGS

In order to understand the invention and to see how it may be carried out in practice, embodiments will now be described, by way of non-limiting examples only, with reference to the accompanying drawings, in which:

FIGS. 3A to 3E are illustrations of different abutments according to the present invention;

FIG. 6A is a perspective exploded view of a dental bridge system according to another aspect of the present disclosed subject matter;

FIG. 6B is an isometric view of the bridge system shown in FIG. 6A, the dental bridge partially cutout;

FIG. 6C is a bottom view of the dental bridge constituting a part of the bridge system shown in FIGS. 6A and 6B;

FIGS. 6D and 6E are perspective bottom and top views, respectively, of a Reduced Bridge-Core constituting a part of the bridge system shown in FIGS. 6A and 6B;

FIGS. 7A to 7D are illustrations of adapter abutment according to another aspect of the present disclosed subject matter for use with the implants of kind shown in FIG. 1;

FIGS. 8A to 8F are bottom perspective views of further examples of adapter abutments;

FIG. 9A is an exploded top perspective view of an abutment fitted with an internal seat coupler and a fastener screw;

FIG. 9B is an assembly of FIG. 9A; and

DETAILED DESCRIPTION OF EMBODIMENTS

Figure 1A:
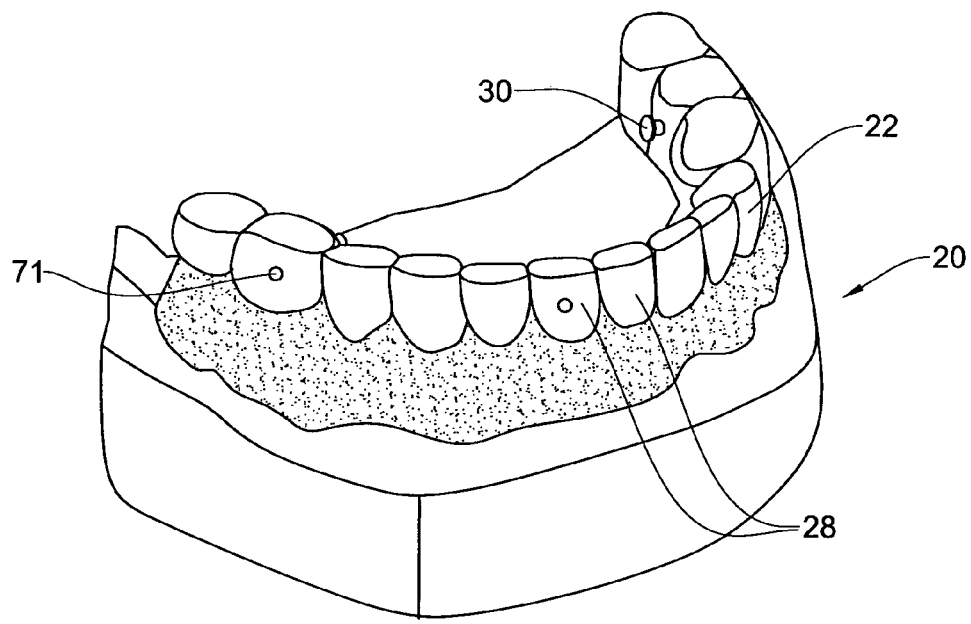
FIG. 1A is a front perspective view of a dental bridge system according to a first aspect of the present disclosed subject matter, at an assembled position.
Figure 1B:
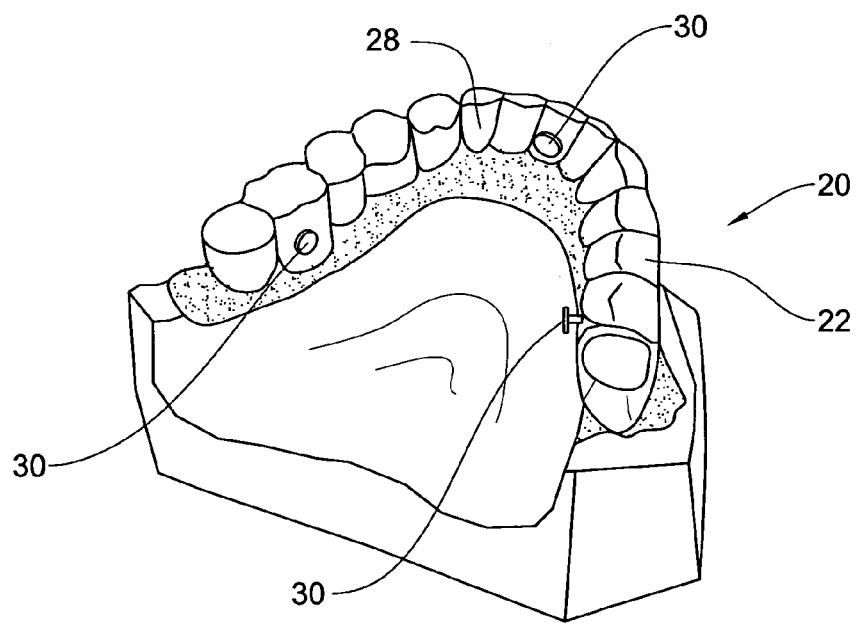
FIG. 1B is a rear perspective view of a dental bridge system of FIG. 1.
Figure 1C:
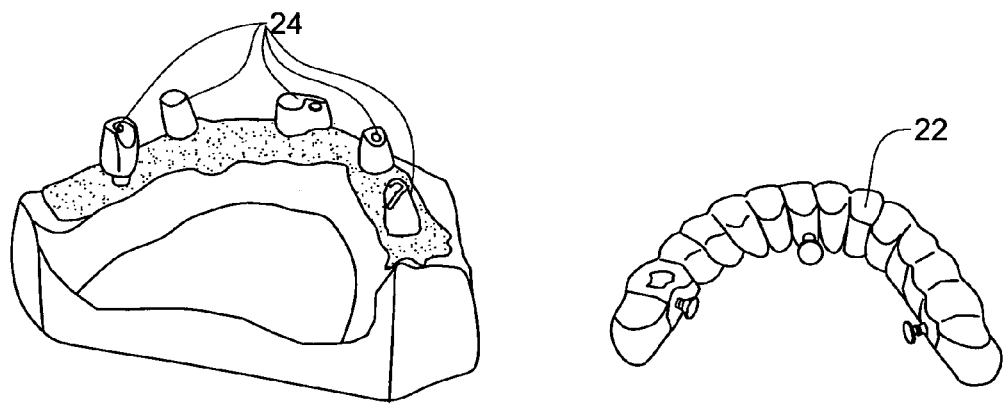
FIG. 1C is a rear perspective view of the dental bridge system of FIG. 2, with the bridge removed from the jaw.
Figure 1D:
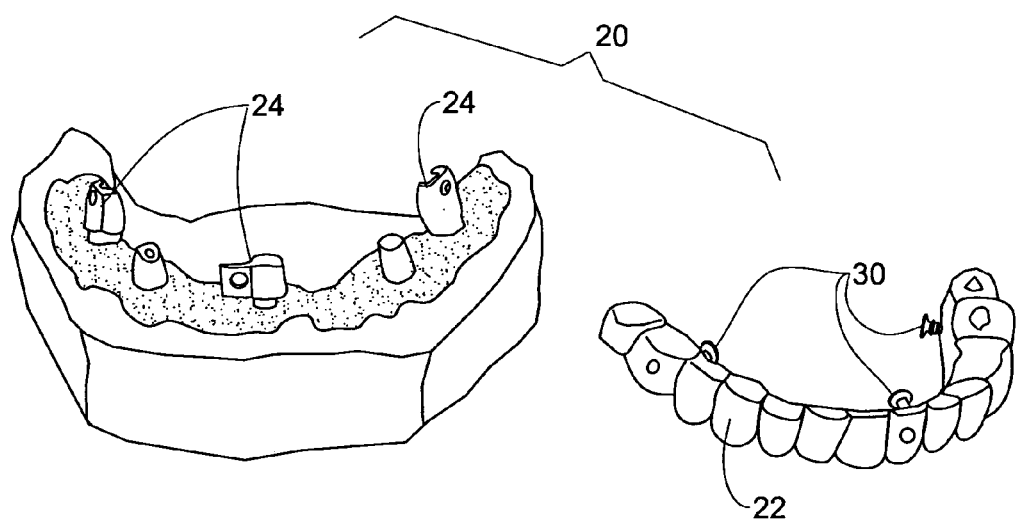
FIG. 1D is a front perspective view of the dental bridge system of FIG. 2, with the bridge removed from the jaw.
Figure 1E:
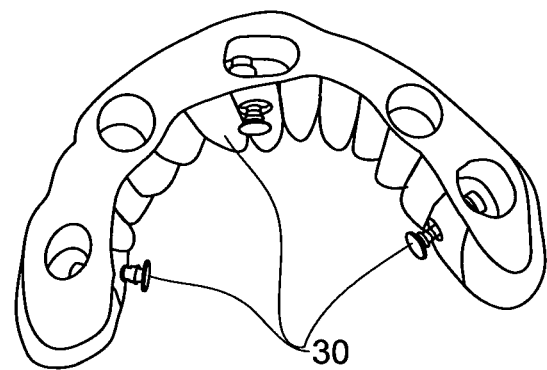
FIG. 1E is a rear bottom view of the dental bridge illustrated in FIGS. 1A to 1D, with the locking members at their open, unlocked position.
Figure 1F:
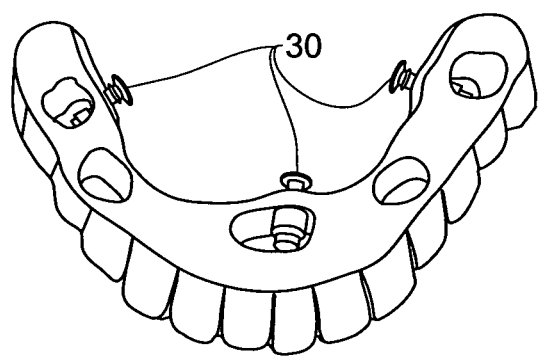
FIG. 1F is a front bottom view of FIG. 1E.

With reference to FIGS. 1A to 1G there is illustrated a bridge system according to a first aspect of the present disclosed subject matter, generally designated 20, comprising a dental bridge 22, a plurality of abutments generally designated 24 (FIGS. 1C, 1D and 1G) secured over dental implants generally designated 26 (FIG. 1G) and locking arrangements generally designated 30. A dental bridge is at times referred to merely as bridge.

The dental bridge 22 is an integrated array of artificial teeth 28 (with substantially no real gaps therebetween), mimicking the natural lost teeth of a individual, i.e. follows the individual's anatomic parameters, such as shape, size, color etc., and conforming with resident natural teeth or artificial teeth of the individual, however without a skirt portion i.e. a gum mimicking portion (at times referred to as an 'acrylic flange'). The dental bridge is made of any rigid and hard metallic or non-metallic material (such as, for example, metals—gold, titanium, chrome-cobalt, zirconium, porcelain, plastic/acrylic/polymeric materials, composite materials, and combinations thereof), molded or machined or composited of several materials and layers.

Figure 1G:
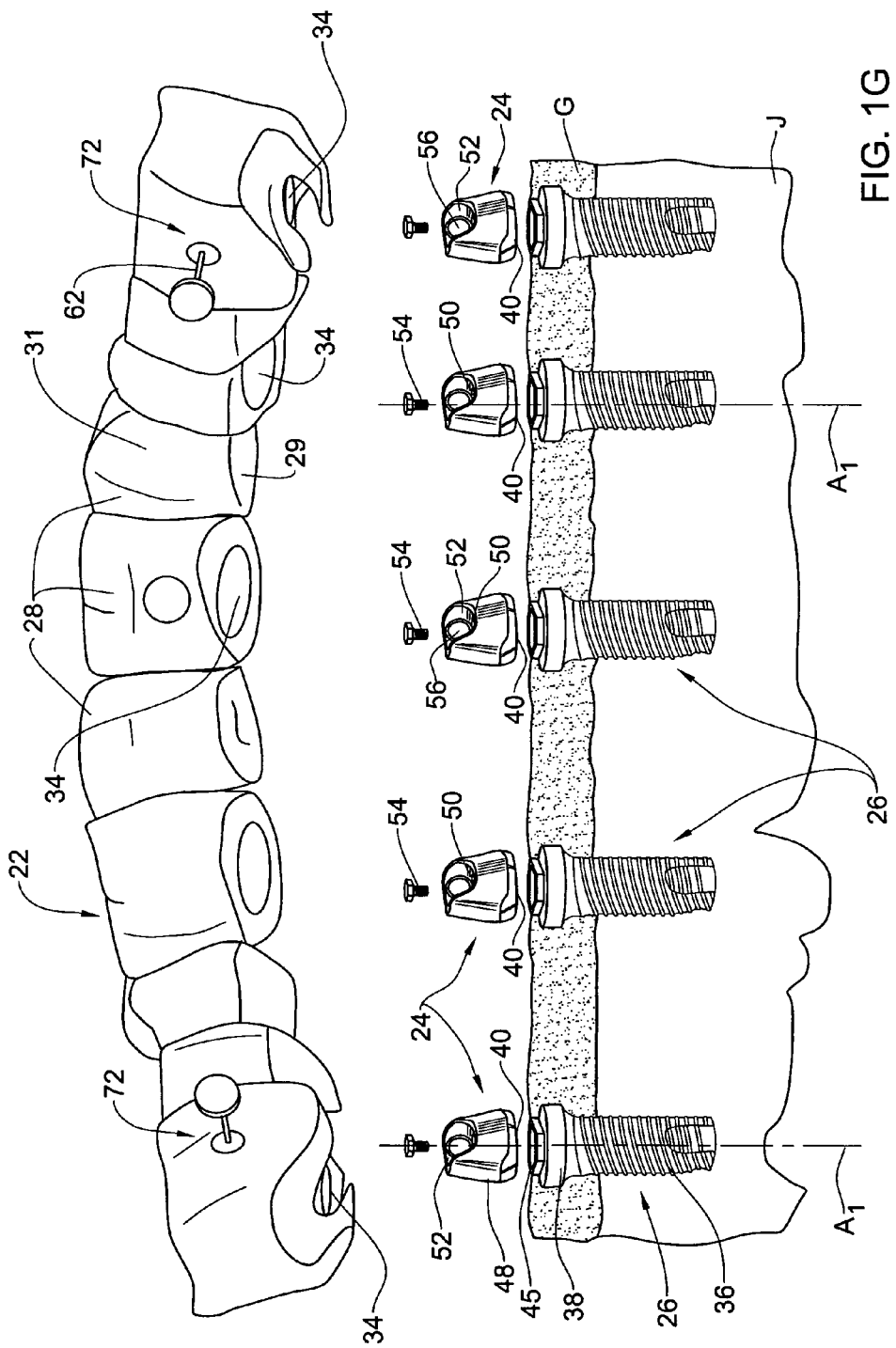
FIG. 1G is a rear exploded view of the dental bridge system of FIG. 1A, with the locking members at their open, unlocked position.

With reference to FIG. 1G, the bridge 22 comprises a bottom surface 29 and an inside face (lingual or palatal wall) 31 generally upright extending from the bottom surface 29. The bottom surface 29 is configured with a plurality of receiving apertures 34, each formed for precision fit (substantially no movement therebetween) over at least a major portion of a corresponding abutment 24, as detailed below.

The dental implants 26, typically made of metal, are each configured with a body portion 36 and a head portion 38, and extend about a longitudinal axis $A_1$. The body portion 36 of the dental implants 26 is fixedly received within jawbone J of an individual and extends through the gum tissue G such that implant head 38 projects there through. Each implant head 38 comprises an upward extension 45 of a hexagonal shape, as shown in FIG. 1, or any other shape, as will be discussed hereinafter in connection with other examples.

Each of the abutments 24 is configured for fixedly securing to a respective implants 26, and for that purpose each abutment 24 comprises a seat portion 40 having a receptacle 42 (FIGS. 2B and 2C) formed with an inner shape conforming with the outer shape of the extension 45 of the implant head 38, so as to allow the abutment 24 to fixedly engage the corresponding implant head 38, i.e. with substantial no respective movement therebetween. The inner shape of the receptacle 42 may be a hexagon (FIG. 2B) or any polygonal shape such as an octagon, a square, a triangle, a rectangle or any irregular shape that conforms with the shape of the upward extension 45 of the implant head 38, so as to ensure fixed positioning of the abutment 24 over the implant 26, and substantial no movement therebetween.

The abutment 24 is further configured with an abutment head 48, designed for snugly fitting within the corresponding aperture 34 configured at the bottom surface 29 of the bridge 22. The abutment head 48 of at least several of the abutments 22. (or all) is formed with a lock cradling portion 52 configured to receive a lock housing 70 of a lock mechanism 72 as will be discussed hereinafter in connection with FIG. 4. The lock cradling portion 52 is configured, according to a particular example, to embrace a significant portion of the respective lock housing, thereby increasing and improving the tight fit of the bridge 22 over the abutments 24. The cradling portions 52 are formed with a locking pin arresting portion 56, which in the present example is a through going bore, extending substantially coaxial with a locking pin 62 of the lock mechanism 72.

The abutment head 48 further comprises a through going bore 50 (FIGS. 1G and 2A to 2C), extending along the abutment head 24, for screwing therein an abutment screw 54 for fixedly securing the abutment 24 to the implant 26, in a fashion assuring no movement therebetween.

The abutments 24 are made of any rigid and hard metallic or non-metallic material (such as, for example, metals—gold, titanium, chrome-cobalt, zirconium, porcelain, plastic/acrylic/polymeric materials, composite materials, and combinations thereof), molded or machined or composited of several materials and layers.

Figure 2A:
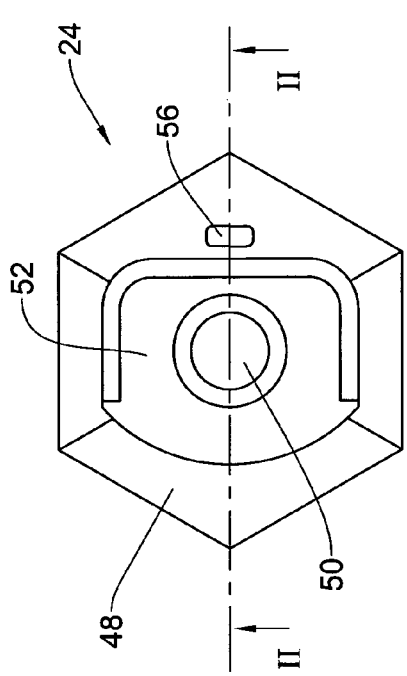
FIG. 2A is a schematic top view of an abutment constituting part of the bridge system shown in FIG. 1A.
Figure 2B:
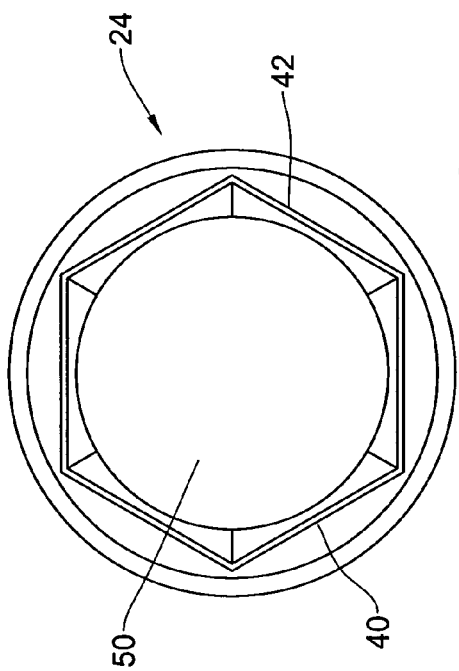
FIG. 2B is a schematic bottom view FIG. 2A.
Figure 2C:
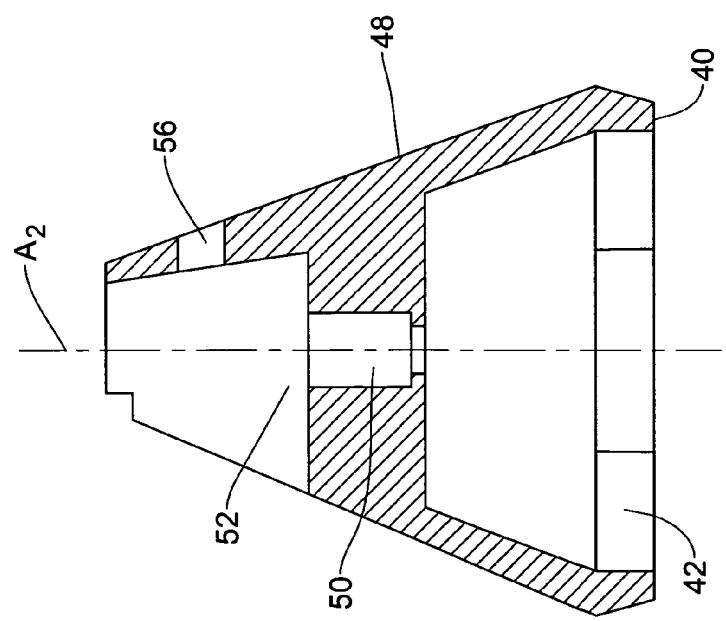
FIG. 2C is a schematic cross-sectional view taken along a plane designated by line II-II in FIG. 2A.

The abutment 24 illustrated in FIGS. 2A to 2C is configured such that the seat portion 40 and the head portion 48 have a coextending axis $A_2$ which upon mounting over the implant head 38 coextends with the axis $A_1$ of the implant 26. This however is a particular example which as will be disclosed in connection with some of the drawings, may be different.

It is further appreciated that the number of locks 72 may change, depending on different parameters such as space, strength of material, accessibility thereto by the individual, etc. it is also noted that one or more of the abutments may be regular abutments, i.e. not configured with a locking portion of at least one of said abutments is configured as a locking abutment and comprises a locking portion 52 (cradling portion 52). Thus, where for some reason it is required to provide fewer locks (however one or more are required) whilst preparing for optional additional rings, the abutments may be of the type disclosed hereinabove in connection with FIGS. 1 and 2, namely configured the locking portion 52, competent of arresting and supporting the lock housing 72, however without a respective lock fitted at the respective location at the bridge 22.

The locking arrangement generally designated 30 is configured for removably fixing the bridge 22 to the abutments 24. The locking arrangement 30 comprises one or more locks 72 (two locks in the example of FIG. 1), pin-snap type locks in the present example though other forms of locks are possible too, stetting as an example, snap-type locks, swivel-type locks, magnet based locks, locator-type locks, or any other type of locking mechanism.

The locks 72, as can be seen in more detail in FIGS. 4A to 4F is configured with a housing 70 fixedly secured within the bridge 22 e.g. by welding, bonding or otherwise securing, and extending through the rear wall 31 of the bridge 22, and extending into the corresponding receiving aperture 34 of the bridge 22. It is however appreciated that some or all of the locks may be fitted at the front wall (labial face) of the bridge (not shown).

Figure 4A:
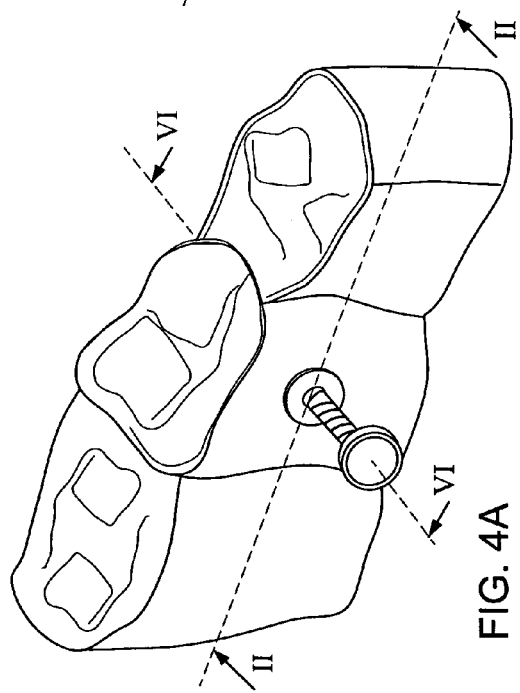
FIGS. 4A and 4B are rear isometric views of a portion of the dental bridge shown in FIG. 1, with a lock mechanism at an open and closed position, respectively.
Figure 4B:
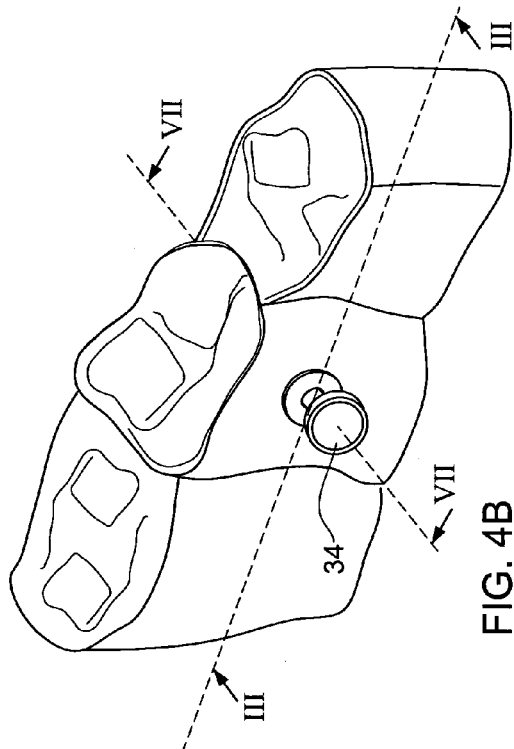
Figure 4C:
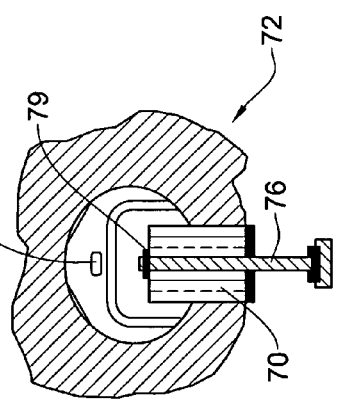
FIGS. 4C and 4D are cross-sectional views taken along planes designated by lines II-II, and III-III- in FIGS. 4A and 4B, respectively.
Figure 4D:
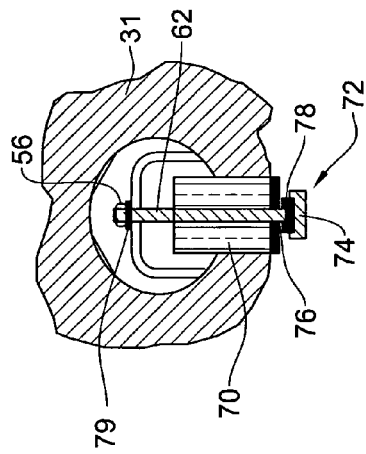
Figure 4E:
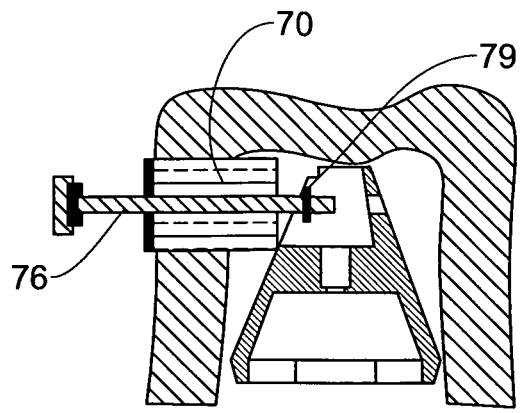
FIGS. 4E and 4F are cross-sectional views taken along planes designated by lines VI-VI, and VII-VII- in FIGS. 4A and 4B, respectively.

The housing serves as a bushing accommodating an axially displaceable locking pin locking pin 62 fitted with a locking portion (extending at the distal end thereof, namely within the receiving aperture 34 of the bridge 22) and formed with an annular limiting ring 79 (FIGS. 4C and 4D) at the end of the locking portion for limiting its displacement through the bushing 70, wherein the locking pin 62 is axially displaceable between a locked position (FIGS. 4B, 4D and 4F) and an open position (FIGS. 4A, 4C and 4E). The locking pin 62 is further formed with a flat grasping disc-like portion 80 at its fore end, to facilitate the extracting of the locking pin 62 by the individual's fingernail or by other means. In addition, an interstice 76 may exist between the rear surface 31 of the bridge and the grasping ring 74 to facilitate the extracting of the locking pin 62. If required, a cushioning and interstice adjusting ring 78 is provided.

As already mentioned hereinabove, the shape and size of the lock's housing 70 is configured such that when a bridge is applied over the abutments, the inside walls of the receiving apertures 34 of the bridge 22 snugly embrace the respective abutments and the respective locking portion 52 (FIG. 1G) receives the housing of the locks to thereby increase the tight and snug fit of the bridge 22 over the abutments 24.

Figure 4F:
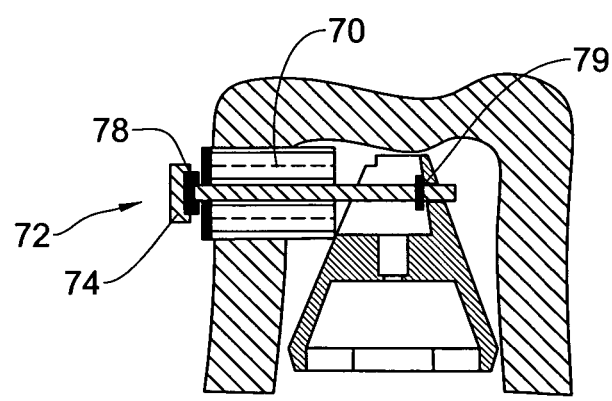

The arrangement is such that after applying and positioning the bridge over the abutments 24, the locking pin 62 is depressed inwards into the position of FIGS. 4B, 4D and 4F, whereby the locking pin 62 engages within the locking pin arresting portion 56 of the abutment 24 within the receiving aperture 34 of the bridge 22. In the open position, upon axially extracting the locking pin 62 into the position of FIGS. 4A, 4C and 4E, the locking pin 62 is extracted so it is no longer arrested by the locking pin arresting portion 56 of the abutment head 24, allowing thereby the removal of the bridge 22.

The load applied through the bridge 22 while chewing is fully born by the abutments 24 and directed to the studs 26 (and further to the jaw bone J), whilst the one or more locks 72 substantially do not bear any loads. Furthermore, the tolerance between the receiving apertures of the bridge and the respective abutment heads is tight, so as to reduce, or substantially eliminate any tolerance and respective motion therebetween.

However, removal of the bridge is facilitated substantially without the need of any tools. It is further appreciated that the locking arrangement is intended rather to prevent unintentional disengagement or removal of the bridge, for example while chewing.

It is further noted that whilst the locking mechanism in itself does not bear loads (i.e. the locking pin, where provided is not subject to any loads), whilst the housing of the locking mechanism may function as a receiving aperture configured for snugly bearing over the locking abutment.

As mentioned above, there may be provided a fine ejection bore (71 in FIG. 1A) extending across the respective abutment and the dental bridge, coaxial with the locking pin, to assist in extracting the pin into the unlocked position, by pushing it inwards using a fine rod (e.g. a paper stapler, etc.)

Turning now to FIGS. 3A to 3D, there are illustrated several examples of abutments according to another aspect of the disclosed subject matter, generally designated 100, 120, 140, 160 and 180, respectively. Each of the illustrated abutments comprises a seat portion designated 102, 122, 142, 162 and 182 respectively, a head portion designated 104, 124, 144, 164 and 184 respectively, and a body portion extending between the seat portion and head portion designated 106, 126, 146, 166 and 186, respectively.

Each of the seat portions defines a seat axis $A_s$ and each of the head portions define an head axis $A_H$, wherein it is noticeable that these axes may coextend (FIGS. 3A, 3B and 3C), or extend parallel to one another (FIG. 3D) or may intersect one another (FIG. 3E).

It is also noted that various modifications are provided for the abutments. For example, the abutment 100 of FIG. 3A is configured such that the abutment head 104 is configured with a laterally extending flange like projection 110, constituting an arresting portion and thus fitted with an aperture 112 for arresting a locking pin of a lock mechanism, not shown.

In the example of FIG. 3B the arresting portion 130 is a significant depression within the body 126 of the abutment, and it is fitted with a radial aperture 132 for arresting a locking pin of a lock mechanism, not shown.

In the example of FIG. 3C the abutment 120 comprises an arresting portion 152A and a through going aperture 152B radially extending through the tubular head portion 144 of the abutment 140.

The abutment 160 exemplified in FIG. 3D is configured with a wide and significant arresting portion designated 170 configured within the body 126 of the abutment, and it is fitted with a radial aperture 172 for arresting a locking pin of a lock mechanism, not shown.

The abutment 180 of FIG. 3E has an inclined configuration and is configured with an arresting portion 182 and a locking aperture 184.

Each of the abutments 100, 120, 140, 160 and 180, has a seat configured for fixedly engagement over a head portion 38 of a dental implants 26 configured with an upward extension 45 (FIG. 1G) having a polygonal shape, or any other shape, to thereby eliminate any movement there between. More so, each of the respective abutment heads further comprises a through going bore (not seen), extending along the abutment, for screwing therein an abutment screw (not shown) for fixedly securing the abutment to the implant, in a fashion assuring no movement therebetween.

It is appreciated that the body portion, and at times the head portion and the respective arresting portion of the abutments, are manufactured at high tolerance to provide for tight, snug arresting within the respective receiving aperture formed at the bottom face of the bridge.

An abutment having a non-coaxial configuration between the seat axis $A_s$ and the head axis $A_H$, when fixed on the implant head, the abutment may be oriented in any desired direction with respect to the longitudinal axis $A_1$ of the implant, i.e. it may coextend, or extend parallel to one another (though not coextend), or may intersect one another. The choice of abutments and their positioning/orientation are determined according to the physiological and anatomic parameters of the individual, e.g. face structure, jaw bone dimensions and status, teeth size, gums situation, implant angulation, etc.

Figure 5:
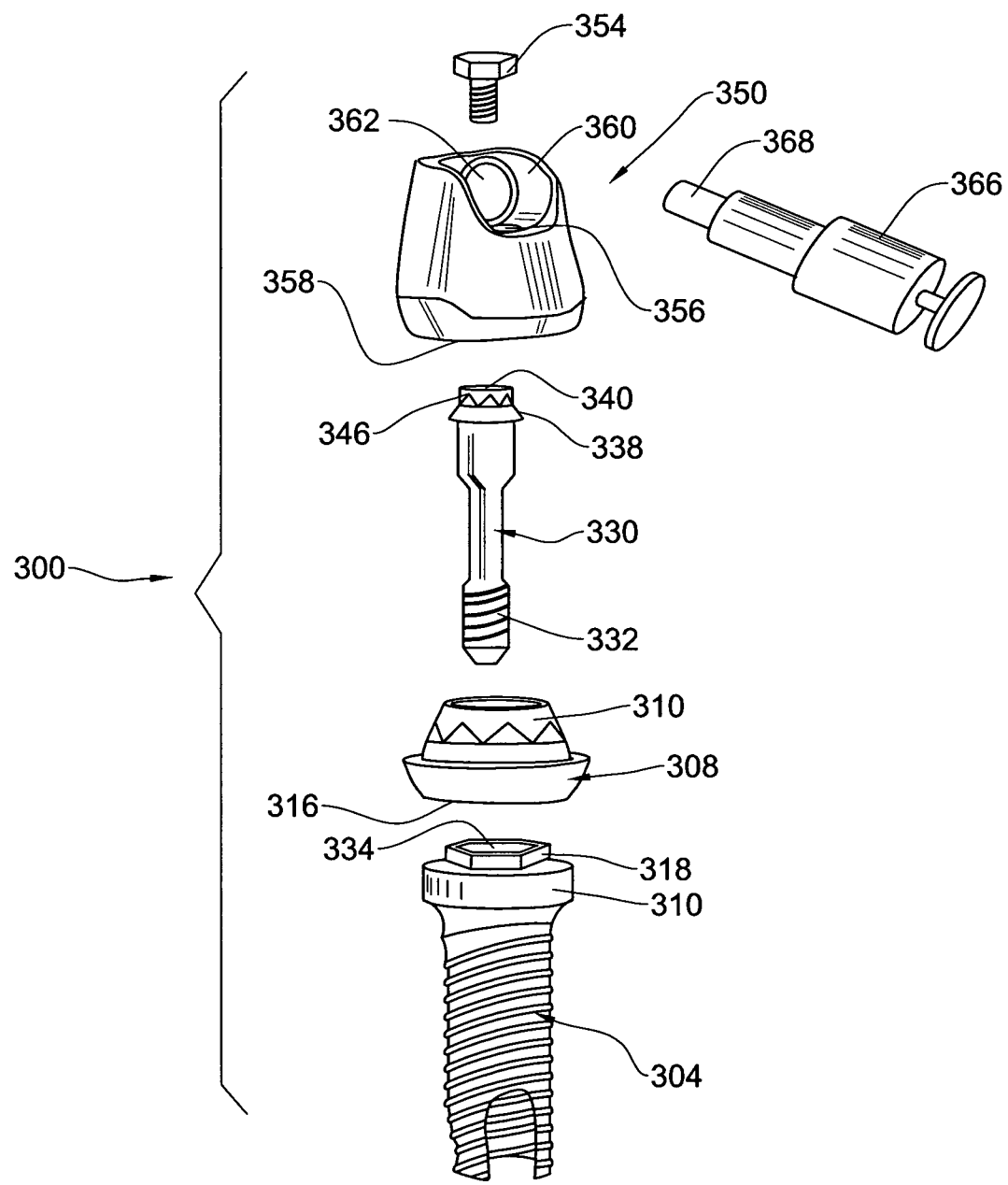
FIG. 5 is an exploded isometric illustration of a dental bridge support system according to another example of the present disclosed subject matter.

With reference now being made to FIG. 5, there is illustrated another example according to the present disclosed subject matter, illustrating a representative fixing assembly collectively designated 300 and composed of a dental implant 304 similar to that disclosed in FIG. 1G, a standard abutment 308 secured over the head portion 310 of the implant 304, wherein the abutment is configured with a seat portion 316 conforming in shape that of the upward extending external polygonal connection support 318, and an external crown-like hexagonal forming 310. The abutment 308 is fixedly secured to the dental implant 304 by a screw 330 configured with a threaded stem portion 332 engageable by a threaded bore 334 of the implant 304.

A head portion 338 of the screw 330 is configured with a threaded bore 340 and an external connection crown-like portion 346. An adapter abutment 350 is provided and is secured over the standard abutment 308. This is facilitated by a fixing screw 354 extending through an axial bore 356 of the adapter abutment 350 and fixedly engageable within the threaded bore 340 of screw 330. A bottom portion of the adapter abutment 350 (not seen) is configured with a receiving aperture 358, formed with hexagonal walls corresponding with those of the crown-like portion 310 of the standard abutment 308, whereby the adapter abutment 350 may be fixedly positioned at any desired angular setting.

The adapter abutment 350 is further configured with a locking pin arresting portion 360 and a pin arresting aperture 362 designed for arresting a locking pin 366 and the locking pin 368, respectively.

The above configuration facilitates for extending (elongating) the implant to a desired height and at a desired angle with respect to the implant, so as to allow convenient fixation of elements such as abutments and unitary braces described above, or other elements adapted to be fixed on the dental implants Noticeable, the arrangement disclosed in FIG. 5 is such that the relative positioning between the standard abutment 308 and the implant 304, and further between the standard abutment 308 and abutment 350 facilitates practically an unlimited range of angular and elevation positioning, to thereby provide a most suitable fitting for the bridge, in spite of various special dental conditions of the individual, as mentioned hereinabove. Setting the relative position between the standard abutment 308 and the implant 304, and further between the standard abutment 308 and abutment 350 takes place by internal or external positioning formations ('internal connection', 'external connection'), however not limited to any particular shape, i.e. regular or irregular shapes.

Further attention is now directed to FIGS. 6A to 6D, illustrating a removable bridge system according to another aspect of the present disclosed subject matter, generally designated 400. The bridge system 400 comprises a Super Dental-Bridge 404, a Reduced Bridge-Core 408 a set of dental implants 450 secured within the jaw bone J and projecting above the gums G (FIG. 6B). In the particular example of FIGS. 6A and 6B there is further provided a locking arrangement comprising two pin-type locks designated 414.

The Super Dental-Bridge 404 is integrated with a plurality of teeth 418 generally conforming with dental parameters of the individual, so that the teeth 418 mimicking the individual's natural teeth as far as shape, size, color etc. The term integrated suggests that the teeth are continuous i.e. are attached to one another though interstices may show. The bridge is made of any rigid and hard metallic or non-metallic material (such as, for example, metals—gold, titanium, chrome-cobalt, zirconium, porcelain, plastic/acrylic/polymeric materials, composite materials, and combinations thereof), molded or machined or composited of several materials and layers.

The Super Dental-Bridge 404 is configured with a rear (lingual) face 420, a front (labial) face 422 and as bottom surface 426 (FIG. 6C) formed with a recess 428 extending substantially the entire length of the bridge 404 for receiving therein the bridge core 408. The Super Dental-Bridge 404 is fitted with a plurality of locks 414 embedded within the rear wall 420.

The Reduced Bridge-Core 408 is made of any rigid metallic or non-metallic material (such as, for example, metals—gold, titanium, chrome-cobalt, zirconium, porcelain, plastic/acrylic/polymeric materials, composite materials, and combinations thereof), molded or machined or composited of several materials and layers. The Reduced Bridge-Core 408 is formed with several thoroughgoing bores 432 (extending at an upright plane) from a top surface thereof 434 (FIG. 6E) to a bottom surface 436 thereof (FIG. 6D). The bottom surface 436 is configured with depressions suited for receiving head portions of the abutments 450 projecting from the gums (FIG. 6A), and the thoroughgoing bores 432 facilitate to fixedly secure the Reduced Bridge-Core 408 over the abutments 450 by screws 438, which abutments are in turn are secured to the studs (not seen). However, according to another example, the Reduced Bridge-Core may be fixed directly to the studs or via adapter abutments, as may be the case. Noticeably, the Reduced Bridge-Core 408 may be secured directly over the implants (not shown).

The Super Dental-Bridge 404 and the Reduced Bridge-Core 408 are shaped and sized conjointly i.e. such that the bridge fits at fit tolerance over the Reduced Bridge-Core, with substantial no tolerances therebetween, to thereby substantially eliminate any relative displacement therebetween.

According to a first example (FIG. 6C), the Super Dental-Bridge 404 does not comprise any locks and thus fixation of the Super Dental-Bridge to the Reduced Bridge-Core 408 takes place by applying an adhesive or bonding material therebetween, upon curing of which the Super Dental-Bridge becomes fixedly attached over the Reduced Bridge-Core and removal thereof is facilitated by breaking the adhesive layer (this operation is usually performed by a professional). According to yet an example, the bridge comprises several openings 440. In the particular illustration of FIG. 6C they are all performed on the top surface of the Super Dental-Bridge, though in practice such openings are performed in an alignment with corresponding threaded bores formed in the Reduced Bridge-Core or in alignment with screws 438 serving to fix the Reduced Bridge-Core to the abutments, whereby the openings may be formed at various locations of the bridge. Once fixed to the Reduced Bridge-Core by the screws, the openings 440 are disguised and sealed whereby removal of the Super Dental-Bridge is usually performed by a professional.

The Reduced Bridge-Core 408, according to one of its examples, is shaped so as to generally follow the shape of the individual's natural teeth, though at reduced scale. This arrangement results in a small Reduced Bridge-Core 408, resulting in that the bridge need not be too large either, thus rendering it suitable also for individuals having small face structure. However, the bridge snugly mounts over the Reduced Bridge-Core, embracing it (apart of course from the bottom face of the Reduced Bridge-Core), thus providing adequate fit and motion free engagement therebetween, wherein the Reduced Bridge-Core is not noticeable.

In the example of FIGS. 6A and 6B the bridge system 400 is fitted with a locking mechanism in the form of pin-type locks 414, of the type disclosed herein above in connection with FIG. 4, said locks facilitating fixed position of the Super Dental-Bridge over the Reduced Bridge-Core owing to fit tolerance therebetween, and further locking arrangements are provided, to thereby prevent unintentional extraction of the Super Dental-Bridge.

The locks 414 (four in the present example, though any appropriate number of locks is possible), are configured for fixing the bridge over the Reduced Bridge-Core, however permitting it's readily and easy removal by the individual. Yet, it is noted that any loads applied through the Super Dental-Bridge while chewing are fully born by the Reduced Bridge-Core (and through the abutments to the studs and to the respective jaw bone) whilst any one or more locks substantially do not bear any loads. Furthermore, the tolerance between the receiving aperture of the bridge and the respective Reduced Bridge-Core is tight, so as to reduce, or substantially eliminate any tolerance and respective motion therebetween. However, removal of the bridge is facilitated substantially without the need of any tools.

In this example too, the Super Dental-Bridge may be configured with a fine bore extending across the respective Reduced Bridge-Core and the dental bridge, coaxial with the displaceable locking pin, to assist in extracting the pin into the unlocked position, by pushing it inwards using a fine rod. The locks may be configured on either or both the front face and the rear face of the Super Dental-Bridge.

Figure 6F:
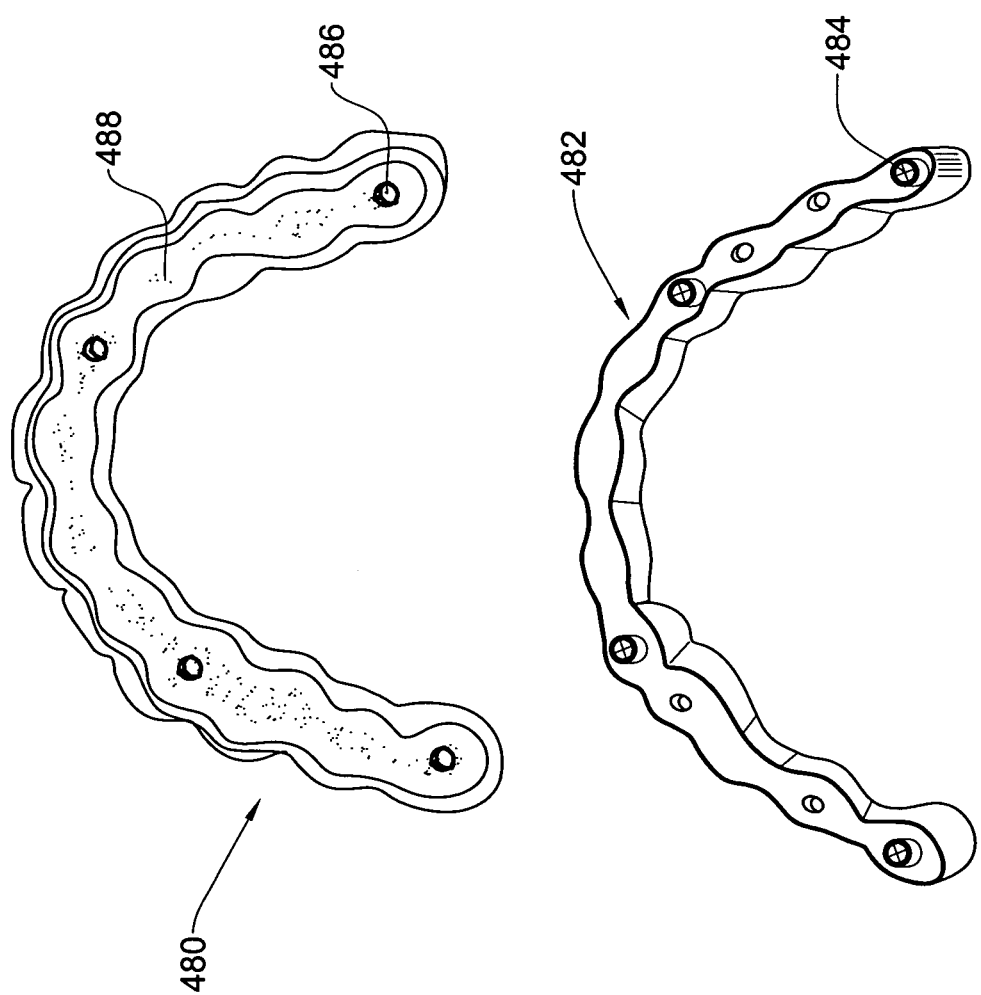
FIG. 6F illustrates a bridge system similar to FIGS. 6A to 6D, however with locator-type locks.

The example of FIG. 6F illustrates a bridge system similar to the example of FIGS. 6A to 6E, however where the Super Dental-Bridge 480 is configured for locking over the Reduced Bridge-Core 482 by locator type locks comprising a plurality of upwardly extending projections 484 projecting from the Reduced Bridge-Core 482 and configured for arresting by receptacles 486 fitted with resilient arresting material and configured at a bottom surface 488 of the Super Dental-Bridge 480.

With further reference now being made to FIGS. 7 and 8 there are illustrated different examples of adapter abutments. Adapter abutments are configured for fixed positioning directly over a stud or over a standard abutment (e.g. regular abutment 308 in FIG. 5), and fixedly supporting a bridge supporting abutment (a regular bridge bearing abutment, such as abutment 350 in FIG. 1G, or a locking abutment, such as abutment 24 in FIG. 1G), i.e. serves as an adjusting coupling element between the bridge supporting abutment and the stud.

The adapter abutments of FIGS. 7A to 7D are generally designated 700, 710, 720, and 730, respectively and are each configured with a seat portion 702, 712, 722 and 732, respectively, and a head portion 704, 714, 724 and 734, respectively.

The base portion of each adapter abutment is configured for fixedly securing over a stud (not shown, however for example of the type shown in FIG. 1G) and thus is configured with a corresponding coupler seat (hexagonal in the present examples), so as to prevent any motion between the stud and the adapter abutment. FIGS. 7A to 7C illustrate an adapter abutment in which the seat is configured with a connector in the form of a female type coupler, i.e. for mounting over a corresponding male seat 706, 716 and 726, respectively (illustrated by dashed lines) of a stud of the type shown in FIG. 1G. FIG. 7D illustrates an adapter abutment in which the seat 736 is configured with a connector in the form of a male type coupler for mounting over a corresponding female type seat of a stud (not shown). A fastener screw 711 is illustrated in FIGS. 7A and 7B for example, for fastening to a stud (or an abetment) through a bore 713 thoroughgoing.

In FIG. 7D the abutment 730 is configured with a downward projecting male-type coupling projection 739 (hexagonal in the present example), designated, for secure fixation of the abutment to a female type receptacle of a stud.

The head portion 704, 714, 724 and 734 of each of the adapter abutments 700, 710, 720, and 730, respectively, is also configured with a connector for coupling to a respective bridge supporting abutment at a fixed, substantially motion less manner. Head connectors 708, 718 and 728 are female type connectors, for supporting a corresponding male type seat connector of the bridge supporting abutment. The head portion 734 of adapter abutment 730 is configured with an external female type connector 738, for supporting a corresponding female type connector of the bridge supporting abutment (not shown).

In the present examples the coupling connectors (708, 718, 728, 738, 706, 716, 726 and 736) are illustrated as regular polygonal shapes. However, the connectors may vary in shape, and size and may be any regular or irregular shape, internal or external (male or female type).

Furthermore, the head portion of each of the adapter abutments may extend at an angle with respect to a corresponding seta portion (FIGS. 7A and 7B) or coaxial with the respective seat portion (FIGS. 7C and 7D).

The provision of adapter abutments is desired for one or more of the following reasons:

Increasing the height of a bridge supporting abutment (i.e. the abutment over which a bridge is received) with respect to a stud;

Changing the angle of a bridge supporting abutment with respect to an axial axis of the stud;

Changing a coupling platform to a bridge supporting abutment;

Changing a coupling platform to a stud;

Interconnecting between different implant systems.

FIGS. 8A to 8F, illustrate further examples of abutments designated 740, 750, 760, 770, 780 and 790 respectively. In these examples the adapter abutments are substantially cylindrical and of same height (this being an example only), and are each configured with a circular head portion 742, 752, 762, 772, 782, and 792 respectively, and an upwardly projecting external connection connector 744, 754, 764, 774, 784 and 794 respectively. The adapter abutments 742, 752, 762, 772 and 782 are each configured also with a circular seat portion 746, 756, 766, 776, and 786 respectively, however, each configured with an internal connection connector differently shaped (pentagon, hexagon, circular, triangular and square, respectively). The abutment 790 of FIG. 8F is fitted at its seat with a downward projecting male-type coupling projection 799 (square in the present example), designated, for secure fixation of the abutment to a female type receptacle of a stud.

FIG. 9A is an exploded top perspective view of an abutment 810 (resembling that illustrated in FIG. 5), however fitted with a hexagonal internal seat coupler 814 projecting at bottom side thereof and a fastener screw 820. FIG. 9B illustrates an assemblage of the abutment 810 and the fastener screw 820.

Figure 10:
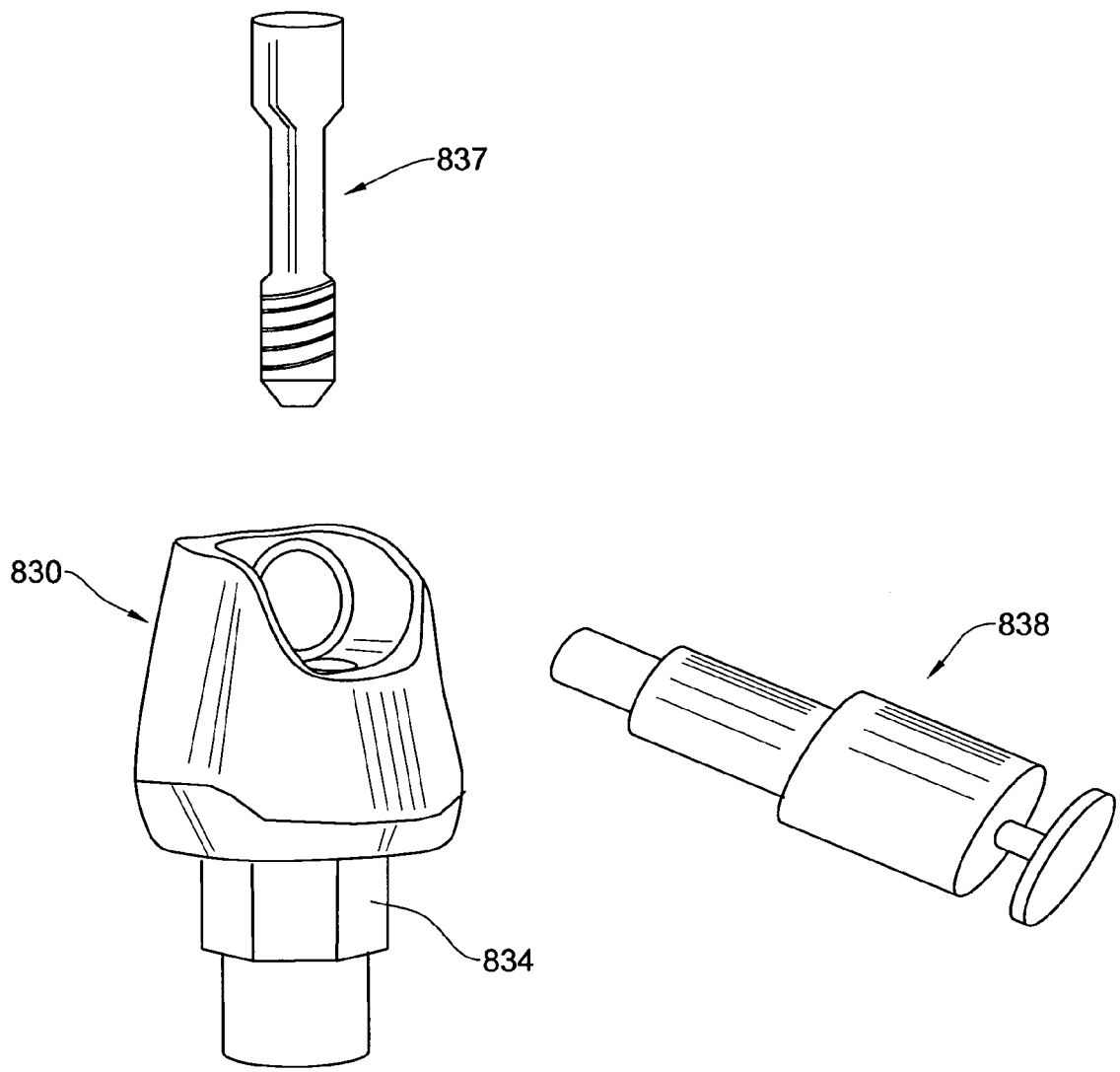
FIG. 10 is an exploded top perspective view of a locking abutment fitted with an internal seat coupler, and a fastener screw and locking member.

FIG. 10 is an exploded top perspective view of a locking abutment 830 fitted with a hexagonal internal seat coupler 834, a fastener screw 837 and a pin-type lock 838, of the type discussed herein above.

Those skilled in the art to which the present disclosed subject matter pertains will readily appreciate that numerous changes, variations, and modifications can be made without departing from the scope of the invention, mutatis mutandis.

The invention claimed is:

1. A removable bridge system for attachment to a plurality of dental implants, each implant having an implant body fixedly receivable inside a jawbone of an individual and an implant head projected from said jawbone, the system comprising:

a plurality of separate and spaced apart abutments, each comprising a seat portion formed with a shape conforming with a shape of a corresponding implant head and allowing fixedly positioning of the abutment to the implant, and an abutment head; at least one of the abutments is configured as a locking abutment and comprises a locking portion;

a bridge generally conforming with dental parameters of the individual, comprising a bottom surface provided with receiving apertures, each receiving aperture shaped so as to snugly fit over at least a portion of a corresponding abutment head; and the bridge further comprises a locking arrangement for removably locking or unlocking the bridge to one or more of the abutments, the locking arrangement comprising one or more locks for releasable locking engagement of the bridge with one or more of the abutments, wherein the locking arrangement is locked without a substantial need for any tools, and wherein a load applied through the bridge while chewing is fully born by the abutments and directed to the implants.

2. The removable bridge system according to claim 1, wherein a housing of the locking arrangement constitutes a receiving aperture configured for snugly bearing over the locking abutment.

3. The removable bridge system according to claim 1, wherein the seat portion of the abutments extends about a fixation bore configured with an inner shape corresponding with an outer shape of the implant head.

4. The removable bridge system according to claim 1, wherein an ejection bore extends across the abutment and dental bridge, coaxial with a locking pin thereof, with an opening for receiving a pushing element to assist in axially displacing said locking pin by sliding into its unlocked position.

5. The removable bridge system according to claim 1, wherein the bridge system is mounted over an adapter abutment to be received between the seat portion of the abutment and the implant head.

6. The system according to claim 1, wherein the locking arrangement comprises one or more axially displaceable pins for sliding and releasable locking engagement with one or more respective abutments, and
wherein the bridge further comprises one or more housing or bushing slidably supporting, respectively, the one or more axially displaceable pins.

7. The system according to claim 1, wherein installing or uninstalling the bridge is facilitated substantially without a need for any tools.

8. The system according to claim 1, wherein the one or more locks are accessible with the tool through a bore or hole in the bridge.

9. The system according to claim 8, wherein the tool is a rod.

10. The system according to claim 1, wherein the one or more locks are each a locking pin configured to be unlocked with use of a tool.

11. A removable bridge system for attachment to a plurality of dental implants, each implant having an implant body fixedly receivable inside a jawbone of a user, the system comprising:
a plurality of separate and spaced apart abutments each connectable to a respective implant;
a bridge comprising receiving apertures for the respective abutments; and
a locking arrangement comprising one or more locks for removably locking and unlocking the bridge to the abutments by the user,
wherein a tolerance between the receiving apertures of the bridge and the respective abutments is tight, so as to reduce, or substantially eliminate any tolerance and respective motion between the receiving aperture and respective abutments,
wherein the locking arrangement is locked or unlocked substantially without a need for any tools, and
wherein the load applied through the bridge while chewing is fully born by the abutments and directed to the dental implants.

12. The system according to claim 11, wherein the locking mechanism comprises a movable locking element.

13. The system according to claim 12, wherein the movable locking element comprises a slidable pin fitted with a grasping portion allowing the user to push or pull on the slidable pin with the user's finger or fingers to, respectively, lock and unlock the locking mechanism.

14. The system according to claim 13, wherein the grasping portion comprises a flat grasping disc-like portion.

15. The system according to claim 12, wherein the bridge further comprises one or more housing or bushing slidably supporting, respectively, the one or more axially displaceable pins.

16. The system according to claim 12, wherein the movable locking element is configured to move in a direction perpendicular relative to a direction of force applied between the bridge and a particular abutment fitted with the locking mechanism during chewing.

17. The system according to claim 12, wherein the movable locking element is configured to move in a direction perpendicular relative to a vertical axis of a particular abutment fitted with the locking mechanism.

18. The system according to claim 11, wherein each receiving aperture of the bridge is shaped so as to snugly fit over at least a portion of a corresponding abutment.

19. The system according to claim 11, wherein the locking arrangement comprises one or more axially displaceable pins for sliding and releasable locking engagement with one or more respective abutments, and
wherein the bridge further comprises one or more housing or bushing slidably supporting, respectively, the one or more axially displaceable pins.

20. The system according to claim 11, wherein each receiving aperture of the bridge is shaped so as to snugly fit over at least a portion of a corresponding abutment.

21. The system according to claim 11, wherein installing or uninstalling the bridge is facilitated substantially without a need for any tools.

22. A removable bridge system for attachment to a plurality of dental implants, each implant having an implant body fixedly received inside a jawbone of a user, the system comprising:
a plurality of separate and spaced apart abutments each connectable to a respective implant;
a bridge generally conforming with dental parameters of the individual, the bridge comprising receiving apertures for the respective abutments; and
a locking arrangement for removably locking and unlocking the bridge to the abutments by manipulation of the locking arrangement by the user,
wherein a tolerance between the receiving apertures of the bridge and the respective abutments is tight, so as to reduce, or substantially eliminate any tolerance and respective motion between the receiving apertures and abutments,
wherein the locking arrangement is locked or unlocked substantially without a need for any tools, and
wherein the load applied through the bridge while chewing is fully born by the abutments and directed to the dental implants.

23. The system according to claim 22, wherein the locking arrangement comprises one or more axially displaceable pins for sliding and releasable locking engagement with one or more respective abutments.

24. The system according to claim 23, wherein the one or more axially displaceable pins is slidable in a direction perpendicular relative a direction of force applied from the bridge to the abutments during chewing movement.

25. The system according to claim 22, wherein the locking arrangement comprises one or more axially displaceable pins for sliding and releasable locking engagement with one or more respective abutments, and
wherein the bridge further comprises one or more housing or bushing slidably supporting, respectively, the one or more axially displaceable pins.

26. The system according to claim 22, wherein each receiving aperture of the bridge is shaped so as to snugly fit over at least a portion of a corresponding abutment.

27. The system according to claim 22, wherein installing or uninstalling the bridge is facilitated substantially without a need for any tools.

28. A removable bridge system for attachment to a plurality of dental implants, each implant having an implant body fixedly receivable inside a jawbone of an individual and an implant head projected from said jawbone, the system comprising:
- a plurality of separate and spaced apart abutments, each comprising a seat portion formed with a shape conforming with a shape of a corresponding implant head and allowing fixedly positioning of the abutment to the implant, and an abutment head; at least one of the abutments is configured as a locking abutment and comprises a locking portion;
- a bridge generally conforming with dental parameters of the individual, comprising a bottom surface provided with receiving apertures, each receiving aperture shaped so as to snugly fit over at least a portion of a corresponding abutment head; and the bridge further comprises a locking arrangement for removably locking or unlocking the bridge to one or more of the abutments, the locking arrangement comprising one or more locks for releasable locking engagement of the bridge with one or more of the abutments,
- wherein the locking arrangement is locked or unlocked substantially without a need for any tools, and
- wherein a load applied through the bridge while chewing is fully born by the abutments and directed to the implants.

29. A removable bridge system for attachment to a plurality of dental implants, each implant having an implant body fixedly receivable inside a jawbone of an individual and an implant head projected from said jawbone, the system comprising:
- a plurality of separate and spaced apart abutments, each comprising a seat portion formed with a shape conforming with a shape of a corresponding implant head and allowing fixedly positioning of the abutment to the implant, and an abutment head; at least one of the abutments is configured as a locking abutment and comprises a locking portion;
- a bridge generally conforming with dental parameters of the individual, comprising a bottom surface provided with receiving apertures, each receiving aperture shaped so as to snugly fit over at least a portion of a corresponding abutment head; and the bridge further comprises a locking arrangement for removably locking or unlocking the bridge to one or more of the abutments, the locking arrangement comprising one or more locks for releasable locking engagement of the bridge with one or more of the abutments,
- wherein the locking arrangement is locked by manipulation of the locking arrangement by the individual without a need for any tools, and
- wherein a load applied through the bridge while chewing is fully born by the abutments and directed to the implants.

* * * * *